(12) United States Patent
Salomone

(10) Patent No.: US 10,143,494 B2
(45) Date of Patent: Dec. 4, 2018

(54) CIRCULAR EXTERNAL FIXATOR

(71) Applicant: MIKAI S.P.A., Genoa (IT)

(72) Inventor: Carlo Salomone, Pietra Ligure (IT)

(73) Assignee: MIKAI S.P.A., Genoa (IT)

( * ) Notice: Subject to any disclaimer, the term of this patent is extended or adjusted under 35 U.S.C. 154(b) by 0 days.

(21) Appl. No.: 14/422,088

(22) PCT Filed: Sep. 13, 2013

(86) PCT No.: PCT/EP2013/002754
§ 371 (c)(1),
(2) Date: Feb. 17, 2015

(87) PCT Pub. No.: WO2014/040738
PCT Pub. Date: Mar. 20, 2014

(65) Prior Publication Data
US 2015/0216564 A1  Aug. 6, 2015

(30) Foreign Application Priority Data

Sep. 14, 2012  (IT) .............................. GE2012A0093

(51) Int. Cl.
*A61B 17/62* (2006.01)

(52) U.S. Cl.
CPC .................. *A61B 17/62* (2013.01)

(58) Field of Classification Search
CPC ....... A61B 17/60; A61B 17/62; A61B 17/645; A61B 17/56; A61B 17/64; A61B 17/6408; A61B 17/6425; A61B 17/6458; A61B 17/6466; A61B 17/6475; A61B 17/6491; A61B 17/66; A61B 2017/567; Y10T 403/33; Y10T 403/335; Y10T 403/645

USPC .......................................................... 606/56
See application file for complete search history.

(56) References Cited

U.S. PATENT DOCUMENTS

| | | | |
|---|---|---|---|
| 3,343,581 A * | 9/1967 | Martin et al. ................ | 411/349 |
| 5,458,599 A * | 10/1995 | Adobbati .......... | A61B 17/7225 606/56 |
| 5,540,686 A | 7/1996 | Zippel et al. | |
| 5,776,132 A * | 7/1998 | Blyakher ....................... | 606/56 |
| 6,030,386 A * | 2/2000 | Taylor ................... | A61B 17/62 606/56 |
| 2005/0240187 A1* | 10/2005 | Huebner et al. ............... | 606/69 |
| 2007/0049930 A1* | 3/2007 | Hearn .................... | A61B 17/62 606/56 |

(Continued)

FOREIGN PATENT DOCUMENTS

| | | |
|---|---|---|
| WO | WO 97/30650 A1 | 8/1997 |
| WO | WO 01/15611 A1 | 8/1999 |

(Continued)

*Primary Examiner* — Jacqueline Johanas
*Assistant Examiner* — Tessa Matthews
(74) *Attorney, Agent, or Firm* — R. Neil Sudol; Henry D. Coleman

(57) ABSTRACT

A circular external fixator, comprising a plurality of rings mutually associated by means of spacer members, each of said rings comprising a plurality of axial bores adapted to engage a fastening means for wire retaining devices. The rings have coupling portions for the connection of the spacer members; each coupling portion has a radial slot adapted to receive a head of one of the spacer member with a snap-on connection.

19 Claims, 6 Drawing Sheets

(56) References Cited

U.S. PATENT DOCUMENTS

| | | | | |
|---|---|---|---|---|
| 2009/0177198 A1* | 7/2009 | Theodoros | ............. | A61B 17/62 |
| | | | | 606/56 |
| 2009/0198234 A1* | 8/2009 | Knuchel et al. | ................ | 606/57 |
| 2011/0200500 A1* | 8/2011 | Feilders | ................... | B01L 7/00 |
| | | | | 422/537 |
| 2012/0123414 A1* | 5/2012 | Steiner | ................... | A61B 17/60 |
| | | | | 606/59 |
| 2014/0058389 A1* | 2/2014 | Singh et al. | .................... | 606/56 |

FOREIGN PATENT DOCUMENTS

| WO | WO 2008/002992 A1 | 6/2007 |
|---|---|---|
| WO | WO 2011/060266 A1 | 11/2010 |
| WO | WO 2011/060264 A1 | 5/2011 |

* cited by examiner

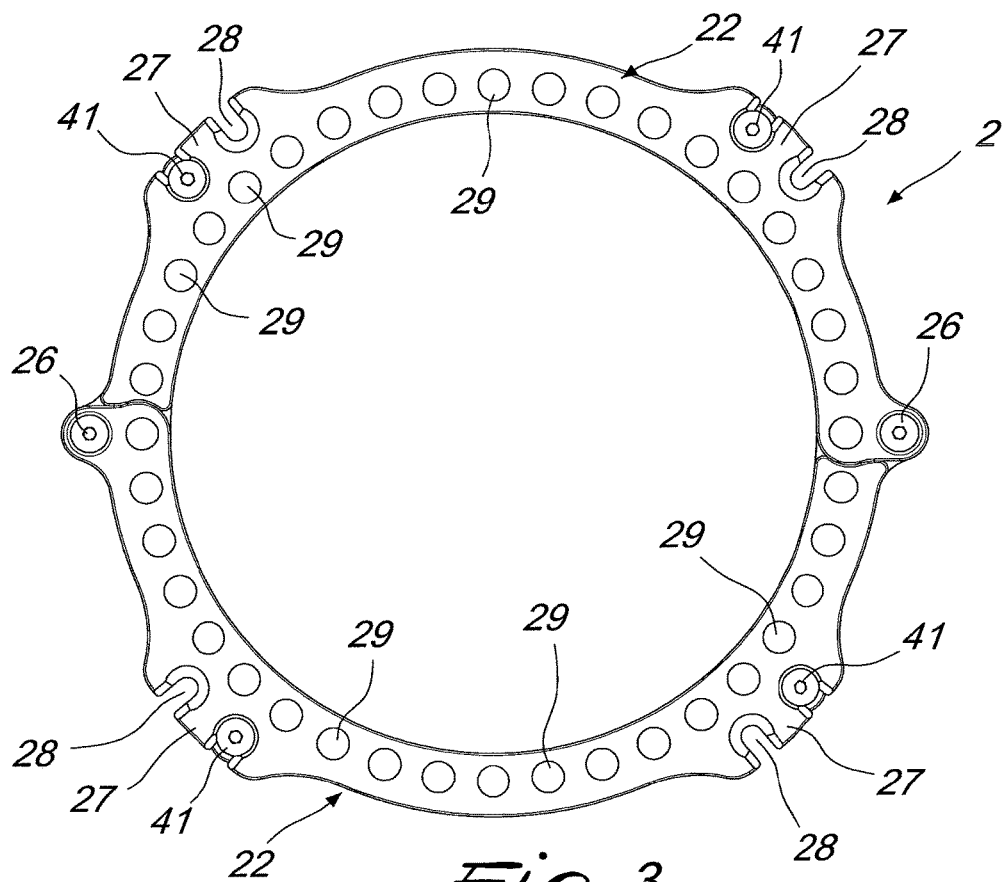
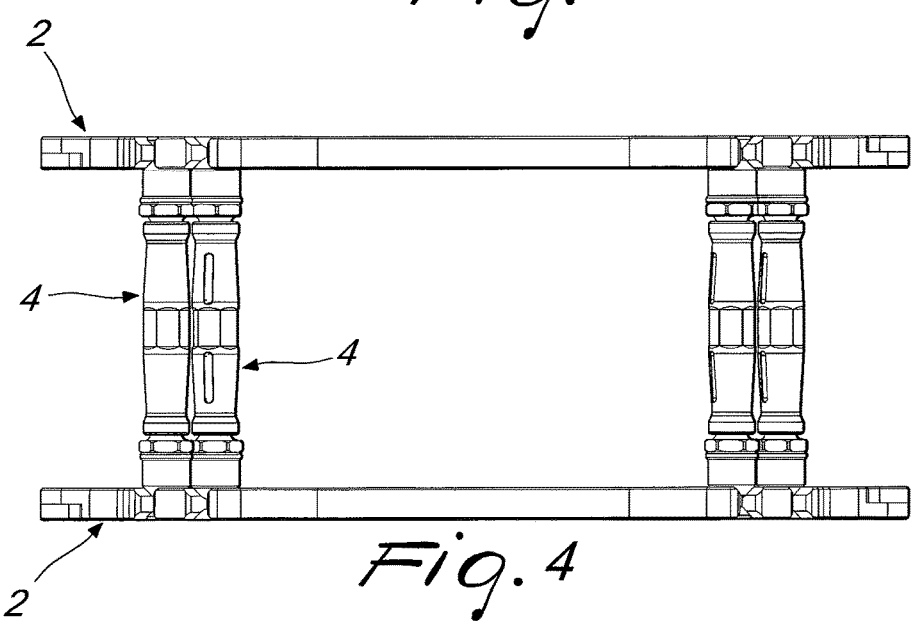

CIRCULAR EXTERNAL FIXATOR

BACKGROUND OF THE INVENTION

The present invention relates to a circular external fixator.

As is known, an external fixator is an external orthopedic device that is fixed to the bone by virtue of metallic wires or pins, which pass through the skin and the soft tissues.

The Ilizarov fixator is a type of fixator having metallic rings that support the bone retention means, i.e., the wires.

A drawback of external circular fixators of the traditional type is that they require a laborious and relatively long assembly.

Another drawback is that the fastening systems and the structural components often constitute an obstruction and an obstacle for the placement of the wires.

Also, any repositioning or reconfiguration of the fixator during surgery is difficult and laborious.

Another problem of traditional systems resides in the difficulty encountered by the patient at home when he has to manually adjust the compression/distraction.

A further drawback of conventional systems is due to the presence of nuts or segments of bars that, particularly when located at the joints of the patient, always cause skin damage and possibly lacerations.

WO2008002992 discloses a radiolucent external fixation element with radio-opaque alignment structures used to form a plane orthogonal to the axis of the bone and center the fixation element upon the axis of the bone.

WO2011/060266 discloses a fixator system having an active strut that can be gradually or acutely adjusted. Adjustments can be made in six degrees of freedom. The passive struts can be rigidly locked or can be unlocked so as to be freely and acutely adjustable while gradual or acute adjustments are made using the one or more active struts.

WO0115611 discloses an orthopedic fixation device in which translation members are secured to adjacent tissue segments for reorientation relative to each other. The device includes telescopically adjustable struts that can be secured to base members by connectors that permit movement of the struts relative to the base members. Rotation of the struts is possible about three axes that intersect at a single coincident point of universal rotation.

OBJECTS OF THE INVENTION

The aim of the present invention is to provide a circular external fixator that overcomes the drawbacks of the cited prior art.

Within the scope of this aim, an object of the invention is to provide a circular external fixator that allows to speed up assembly and make it more versatile even during the intra-operative step, especially if it is necessary to replace members with others having different dimensions.

Another object of the invention is to provide a circular external fixator that offers complete freedom of use of the bores provided in the rings, without obstructions and obstacles on the part of the structural components.

Another object is to provide a circular external fixator that is simple to use even for the patient at home, when he has to correct manually the compression/distraction, with a reduced risk of error.

Another object of the present invention is to provide a structure which, by virtue of its particular constructive characteristics, is capable of giving the greatest assurances of reliability and safety in use.

SUMMARY OF THE INVENTION

This aim and these and other objects that will become better apparent hereinafter are achieved by a circular external fixator, comprising a plurality of rings mutually associated by means of spacer members, each of said rings comprising a plurality of axial bores adapted to engage a fastening means for wire retaining devices; said rings having coupling portions for the connection of said spacer members; said fixator being characterized in that each coupling portion has at least one radial slot adapted to receive a head of one of said spacer member with a snap-on connection.

BRIEF DESCRIPTION OF THE DRAWINGS

Further characteristics and advantages will become better apparent from the description of preferred but not exclusive embodiments of the invention, illustrated by way of non-limiting example in the accompanying drawings, wherein:

FIG. 3 is a plan view of the configuration of the fixator of the preceding FIGURE, in the assembled condition;

FIG. 4 is a front view of the fixator of the preceding FIGURE;

DETAILED DESCRIPTION

Figure 1:
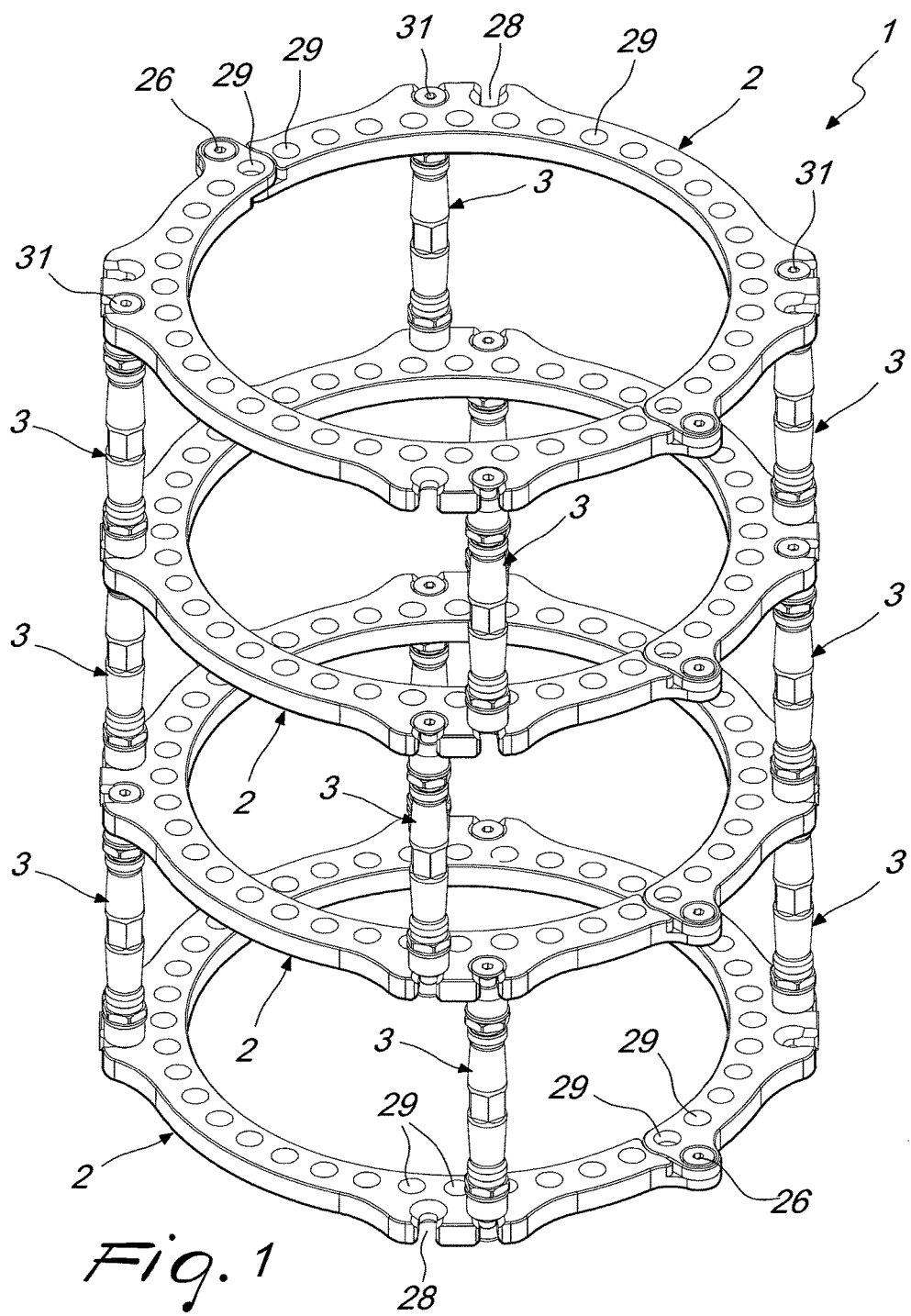
FIG. 1 is a perspective view of an example of configuration of the circular external fixator according to the present invention.
Figure 2:
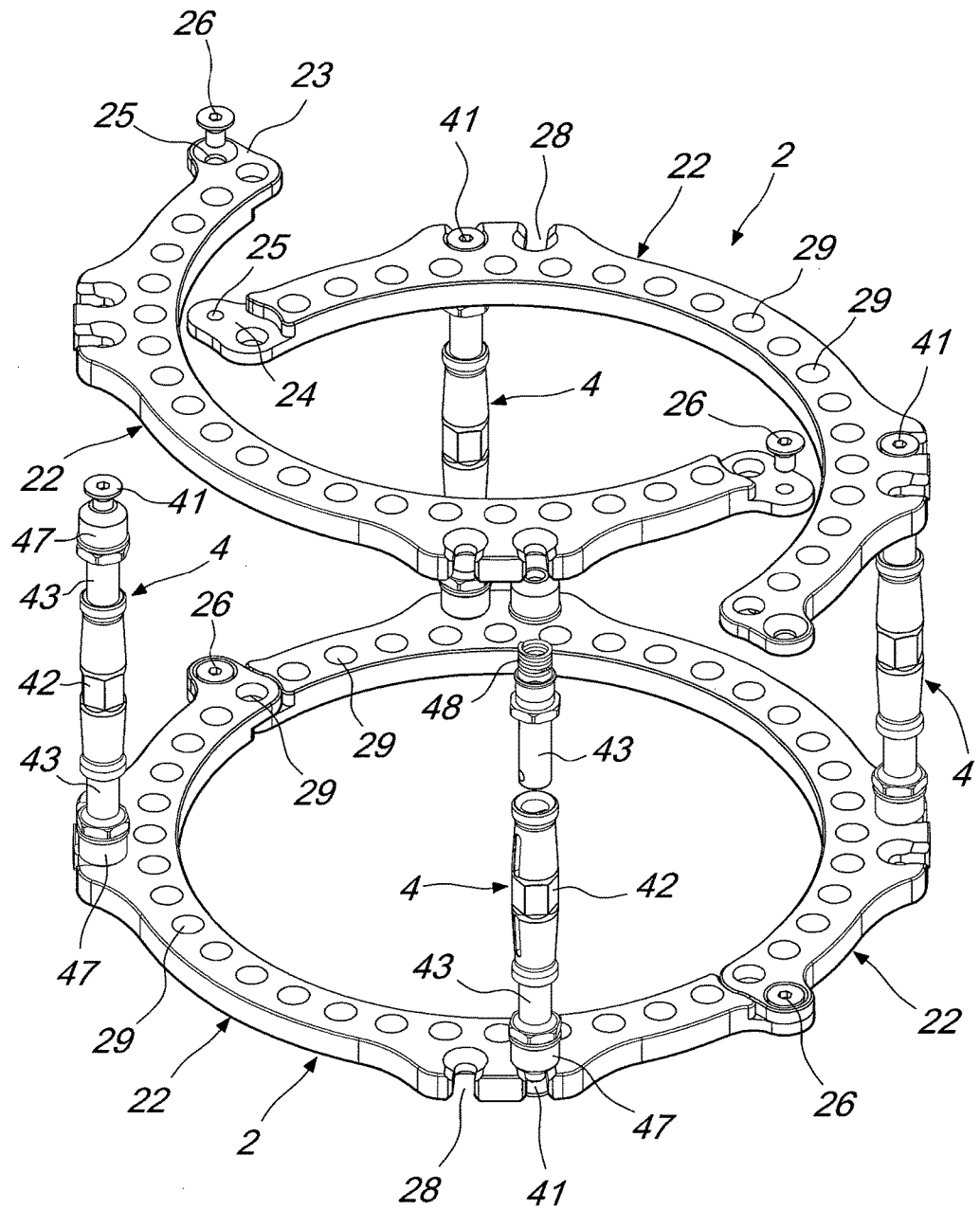
FIG. 2 is a partially exploded perspective view of a pair of rings joined by spacers.
Figure 8:
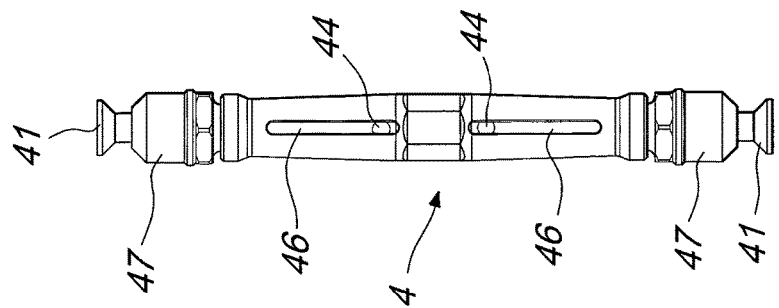
FIG. 8 is a front view of the extendable spacer member of the preceding FIGURE, shown in the assembled condition.
Figure 7:
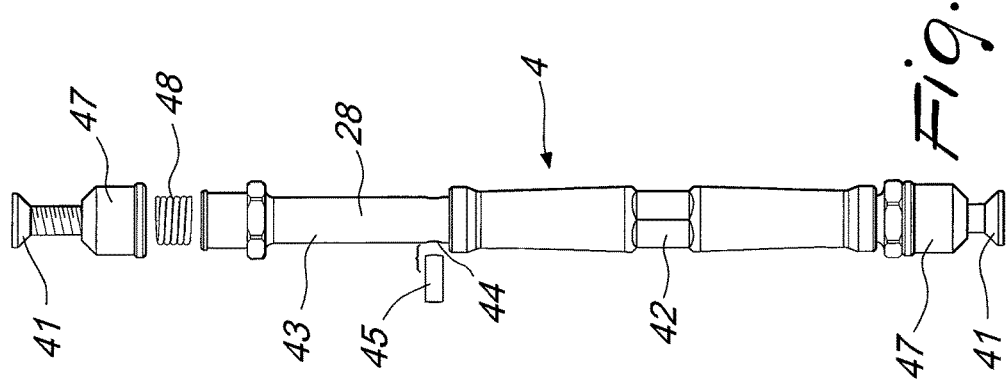
FIG. 7 is an exploded view of an extendable spacer member.
Figure 6:
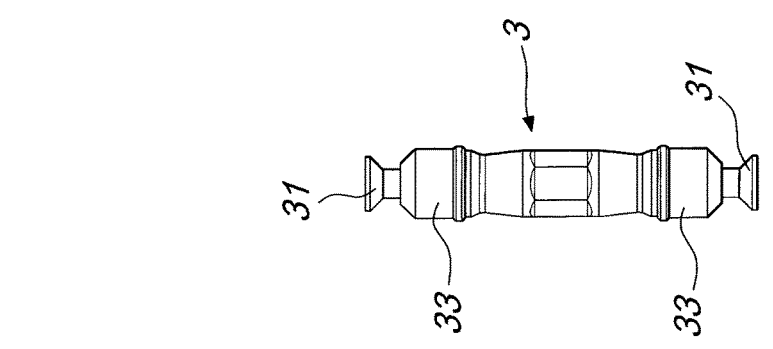
FIG. 6 is a front view of the fixed spacer member of the preceding FIGURE, shown in the assembled condition.
Figure 5:
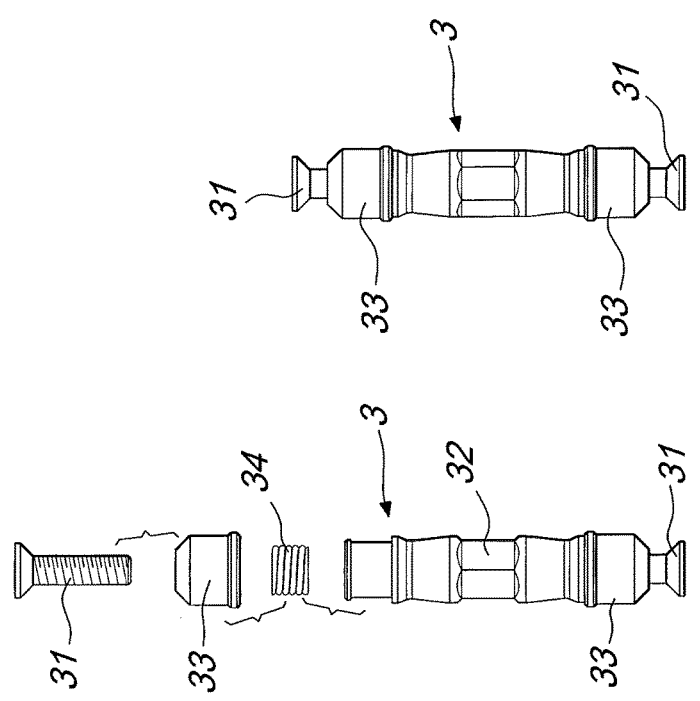
FIG. 5 is an exploded view of a fixed spacer member.
Figure 9:
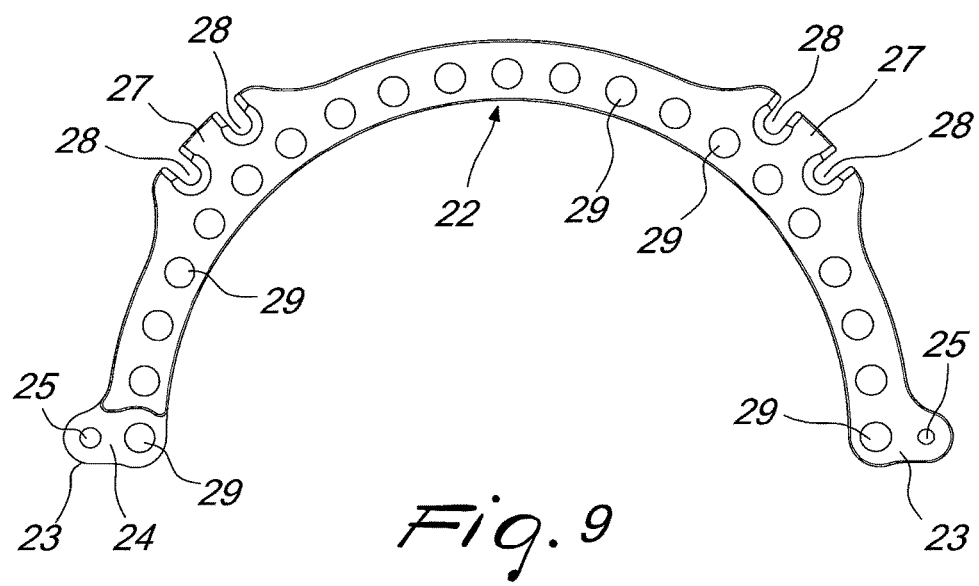
FIG. 9 is a plan view of a semicircular member.
Figure 10:
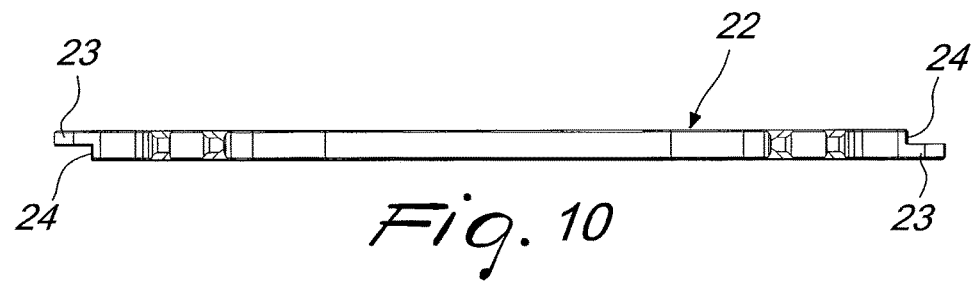
FIG. 10 is a front view of the semicircular member.
Figure 11:
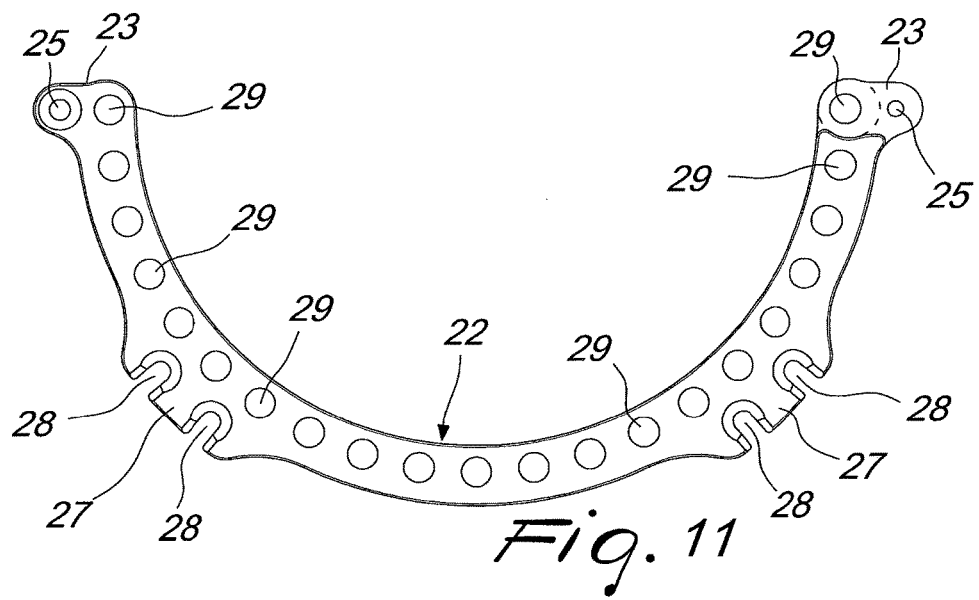
FIG. 11 is a bottom view of the semicircular member.
Figure 12:
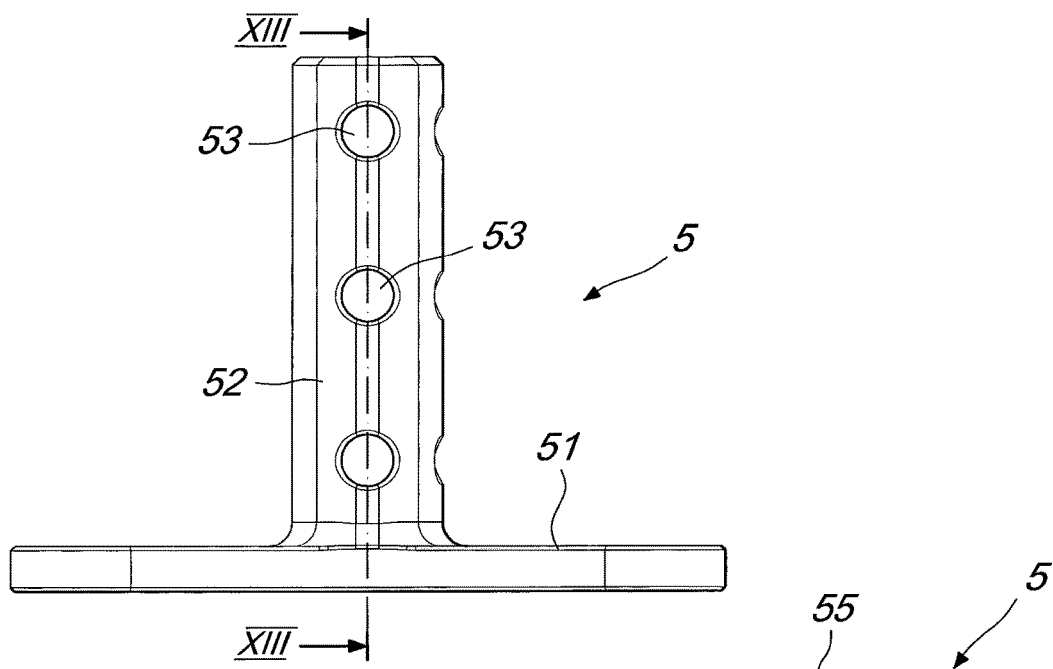
FIG. 12 is a front view of a wire fastening member.
Figure 13:
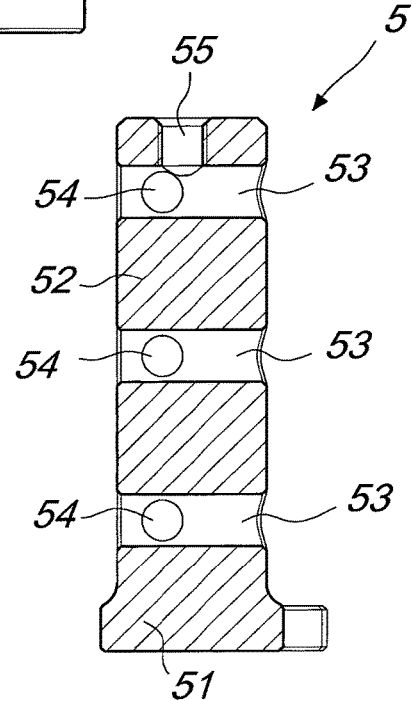
FIG. 13 is a longitudinal cross-section side view of the wire fastening member of the preceding FIGURE.
Figure 14:
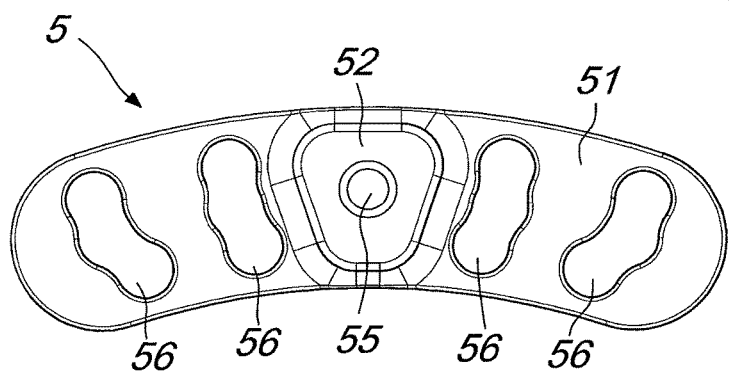
FIG. 14 is a plan view of the wire fastening member of the preceding FIGURE.

With reference to the cited FIGURES, the circular external fixator according to the invention, generally designated by the reference numeral 1, comprises a plurality of rings 2 that are mutually associated by means of spacer members 3 and 4.

Each ring 2 is constituted by two identical semicircles 22 that are joined at their ends.

Each semicircular member 22 has two ends, each constituted by a radially widened portion 23 having a recess 24 provided with a bore 25.

Two semicircles 22 are joined to form the ring 2, whereby the radially widened portions 23 of the ring ends to be joined are superimposed, aligning the respective bores 25 for engagement with a fixing device such as a bolt or screw 26.

Advantageously, the screw 26 has a flat head that rests within the recess 24, without protruding from the surface of the widened portion 23.

The ring ends are configured to be interconnected in order to prevent their disengagement even if the bolt becomes partially loose. This is achieved by the fact that the ends are contoured and partially tuck into each other.

The recess 24 of each radially widened portion 23 is approximately half the thickness of the portion and therefore, once superimposed, the thickness of the joining points between the semicircular members is substantially equal to the overall thickness of the ring 2.

Each ring 2 is provided with coupling portions 27 for the connection of the spacer members 3 and 4.

Each coupling portion 27 has at least one radial slot 28, that is adapted to accommodate a flared flat head screw 31, 41 for fixing a respective spacer member 3 or 4.

Each ring 2 has a set of axial holes 29 that are adapted to receive fixing devices, preferably constituted by flared flat head screws, for fixing wire fastening devices 5.

Each wire fastening device 5 is constituted by a base 51, formed monolithically with an upright 52, and having a plurality of radial seats 53 for the insertion of the wires, that are not visible in the FIGURES.

Each seat 53 has a transverse bore 54 for engagement with a screw for fastening the wire.

The upright 52 has an end bore 55.

The base 51 is provided with a set of slots 56 that can be engaged by flat head screws in order to fix the wire fastening device 5 by virtue of the axial holes 29 of the ring 2.

The fixator is provided with spacers of two types: a fixed spacer 3 and an extendable spacer 4.

The fixed spacer 3 has a fixed bar 32 having two ends provided with plugs 33. Each plug is slidingly connected to its respective end with the interposition of a biasing spring 34, providing a snap-on connection of the spacer 3 to the radial slot 28 of the rings.

The extendable spacer 4 has a central body 42 engaging a threaded bar 43 that has a radial bore 44 for receiving a pin 45.

The pin 45 passes through a longitudinal slot 46 formed in the central body 42.

The free end of the threaded bar 43 is associated with a plug 47 with the interposition of a spring 48 and, similarly, the free end of the central body 42 is associated with a plug 47 with the interposition of a spring, providing a snap-on connection of the spacer 4 to the radial slots 28 of the rings.

The snap-on connection of the spacers 3, 4 allows to connect the spacers to the rings by inserting the spacer ends into the radial slots, without the use of tools. The springs 34, 48 bias the plugs 33, 47 towards the screws 31, 41 thus locking the spacer ends into the radial slots 28.

A spacer 3,4 may be disengaged from the rings by simply pulling the spacer ends out of the radial slots 28. The snap-on connection is of course adjusted in order to prevent any accidental disengagement of the spacer from the rings while allowing its assembling and disassembling without the use of tools.

The circular external fixator according to the present invention is advantageously made entirely of magnetically compatible material.

An advantage of the fixator according to the present invention is that the spacer members that connect the rings do not hinder the possible assembly configurations.

The spacer members are in fact arranged externally to the ring and with a flush profile, and therefore do not obstruct the positioning of the wire fastening devices or of any other accessory, also allowing the use of all the available holes.

The slots for the fixed or extendable spacer members are in fact arranged externally and the heads of the screws 31, 41 are flush with the surface of the rings.

By virtue of the radially widened portions 27, all the bores 29 for positioning the wire fastening devices are available, including those at the spacer members.

The wire fastening devices are provided so as to facilitate their locking; they are in fact provided with the bore 55 on their head, which allows immobilization during fastening with the wrench.

An important and advantageous aspect of the present invention relates to the snap-on connection of the fixed and extendable spacer members that allow for a quick and easy application with respect to the traditional bolt and screw fastening systems.

The snap-on connection allows to easily remove and, if required, replace one or more spacers.

The springs in each spacer also allow for a rather elastic or "dynamic" connection between the spacers and the rings that assists the osseous growth.

According to the invention, the elastic connection may be allowed on all the spacers or adjusted in order to be allowed only on one side of the fixator. The different elasticity of the spacers may be adjusted by using different springs and by the selective tightening of the screws.

These aspects are truly innovative and determine an important and decisive change in the manner of assembly and therefore of use in the operating room of the circular fixator, with a great saving in terms of operating time.

The fixator according to the present invention substantially departs from the prior fixators regarding its construction and installation while maintaining the advantageous anatomical-physiological concepts and principles of pathology treatment, which by now have long been set by the well-established and often imitated Ilizarov fixator.

The exoskeleton of the present fixator can in fact be assembled easily with a small number of quick operations, allowing to provide, depending on the application, any shape depending on the anatomical area to be treated.

This aspect also allows its use in cases that have a multidisciplinary involvement, predominantly plastic surgery, by virtue of the possibility, if necessary, for rapid and specific removal of the bars to be able to perform any additional surgical maneuvers.

In practice it has been found that the invention achieves the intended aim and objects, a fixator having been provided which offers several and substantial advantages with respect to traditional fixators.

The present fixator ensures complete freedom of use of the bores provided on the ring without obstructions and obstacles on the part of the structural components.

The spacer members allow a manual process and, since they are marked in millimeters, simplify the process by not requiring the use of a centimeter ruler.

This is particularly important also for the patient who is at home and has to manually adjust the compression/distraction, with a smaller risk of error.

Differently from traditional fixators, this fixator does not have obstructions caused by nuts or segments of bars that, particularly when located at the patient's joints, always cause skin damage and possibly lacerations.

The composition made of magnetically compatible material ensures that the fixator is extremely lightweight and totally magnetically compatible.

This application claims the priority of Italian Patent Application No. GE2012A000093, filed on Sep. 14, 2012, the subject matter of which is incorporated herein by reference.

The invention claimed is:

1. A circular external fixator, comprising a plurality of rings mutually associated by means of spacer members, each of said rings comprising a plurality of axial bores adapted to engage a fastening means for wire retaining devices; said rings having coupling portions for the connection of said spacer members; a first coupling portion of a first ring having at least one first radial slot with a radially facing opening and adapted to receive a first end of one of said spacer members with a first snap-on connection, said first end of said one of said spacer members comprising a first screw and a first plug, said first plug being slidingly connected with said first end and being biased by a first spring towards a first head of said first screw, to lock said first end into said first radial slot, said first screw comprising a first shaft having a threaded portion and the first head, said first head being connected to one end of said first shaft, said first head being larger than at least a part of said first shaft.

2. The circular external fixator according to claim 1, wherein said spacer members comprise at least one fixed spacer; said fixed spacer having a fixed bar having the first end and at least a second end, said second end having a respective second screw and a respective second plug, said second plug being slidingly connected with the second end and being biased by a second spring towards a second head of said second screw, providing a second snap-on connection of said fixed spacer to a second radial slot, with a radially facing opening, of a second ring, said second screw comprising a second shaft having threaded portion and the second head, said second head being connected to one end of said second shaft, said second head being larger than at least a part of the second shaft.

3. The circular external fixator according to claim 1, wherein said spacer members comprise at least one extendable spacer; said extendable spacer having the first end and at least a second end, said second end having a respective second screw and a respective second plug, said second plug being slidingly connected with the second end and being biased by a second spring towards a second head of said second screw, providing a second snap-on connection of said extendable spacer to a second radial slot, with a radially facing opening, of a second ring, said second screw comprising a second shaft and the second head, said second head being located at one end of the second shaft, said second head being larger than at least a portion of the second shaft.

4. The circular external fixator according to claim 1, wherein said spacer members comprise at least one extendable spacer; said extendable spacer having a central body engaging a threaded bar that has a radial bore for receiving a pin; said pin passing through a longitudinal slot formed in said central body; a free end of said threaded bar having the first screw and the first plug, said first plug being slidingly connected with said bar and being biased by the first spring, providing the first snap-on connection of said extendable spacer to the first radial slot; a free end of said central body having a second screw and a second plug, said second plug being slidingly connected with said central body and being biased by second spring, providing a second snap-on connection of said extendable spacer to a second radial slot, with a radially facing opening, of a second ring.

5. The circular external fixator according to claim 1, wherein each of said rings is constituted by two identical semicircles joined at their ends; each of said ends being constituted by a radially widened portion; said radially widened portion comprising a recess provided with a bore; said radially widened portions of said ends to be joined being superimposed, aligning the respective bores for engagement with a fastener.

6. The circular external fixator according to claim 5, wherein said fastener is a screw fastener having a flat head that rests within said recess, without protruding from the surface of the widened portion.

7. The circular external fixator according to claim 6, wherein the ring ends are contoured and partially tuck into each other, preventing disengagement even if said screw fastener becomes partially loose.

8. The circular external fixator according to claim 7, wherein said recess of each radially widened portion is approximately half the thickness of the portion so that a combined thickness of superimposed radially widened portions of the semicircles is substantially equal to the overall thickness of the respective ring.

9. The circular external fixator according to claim 1, wherein each wire retaining device comprises a base that is formed monolithically with an upright, which comprises a plurality of radial seats for the insertion of wires; each seat has a transverse bore for engagement with a screw, for fastening the wire; said upright having a top bore; said base having a series of slots that can be engaged by screws for fastening the wire retaining device by virtue of the axial bores of the rings.

10. The circular external fixator according to claim 1, wherein each of said rings has a respective outer profile or edge, said at least one radial slot being open toward the respective outer profile or edge.

11. The circular external fixator according to claim 1, wherein each of said rings has a respective first axis and a respective radially outer surface extending parallel to the first axis of the respective ring; said radially facing opening being disposed in the radially outer surface of the respective ring; the axial bores having respective second axis parallel to said first axes.

12. A circular external fixator, comprising a plurality of rings mutually associated by means of spacer members, each of said rings comprising a plurality of axial bores adapted to engage a fastening means for wire retaining devices; said rings having coupling portions for the connection of said spacer members; a first coupling portion of a first one of said rings having at least one first radial slot with a radially facing opening and which is adapted to receive a first end of one of said spacer members with a first snap-on connection, said first end of said one of said spacer members comprising a first screw and a first plug, said first plug being slidingly connected with said first end and being biased by a first spring towards a first head of said first screw, to lock said first end into said first radial slot, said first spring being a compression spring disposed on a side of said first plug opposite said first head of said first screw.

13. The circular external fixator according to claim 12, wherein said spacer members comprise at least one fixed spacer; said fixed spacer having a fixed bar having the first end and at least a second end, said second end having a respective second screw and a respective second plug, said second plug being slidingly connected with said second end and being biased by a second spring towards a second head of said second screw, providing a second snap-on connection of said fixed spacer to a second radial slot, with a radially facing opening, of a second one of said rings.

14. The circular external fixator according to claim 12, wherein said spacer members comprise at least one extendable spacer; said extendable spacer having the first end and at least a second end, said second end having a respective second screw and a respective second plug, said second plug being slidingly connected with said second end and being biased by a second spring towards a second head of said second screw, providing a second snap-on connection of said extendable spacer to a second radial slot, with a radially facing opening, of a second one of said rings, said second screw comprising a shaft and said second head, said second head being located at one end of said shaft, said second head being larger than at least a portion of said shaft.

15. The circular external fixator according to claim 12, wherein said spacer members comprise at least one extendable spacer; said extendable spacer having a central body engaging a threaded bar that has a radial bore for receiving a pin; said pin passing through a longitudinal slot formed in said central body; a free end of said threaded bar having said first screw and said first plug, said first plug being slidingly connected with said bar and being biased by said first spring, providing the first snap-on connection of said extendable spacer to said first radial slot; a free end of said central body having a second screw and a second plug, said second plug being slidingly connected with said central body and being biased by a second spring, providing a second snap-on connection of said extendable spacer to a second radial slot, with a radially facing opening, of a second one of said rings.

16. The circular external fixator according to claim 12, wherein each of said rings is constituted by two identical semicircles joined at their ends; each of said ends being constituted by a radially widened portion; said radially widened portion comprising a recess provided with a bore; said radially widened portions of said ends to be joined being superimposed, aligning the respective bores for engagement with a fastener.

17. The circular external fixator according to claim 16, wherein said fastener is a screw fastener having a flat head that rests within said recess, without protruding from the surface of the widened portion.

18. The circular external fixator according to claim 17, wherein the ring ends are contoured and partially tuck into each other, preventing disengagement even if said screw fastener becomes partially loose.

19. The circular external fixator according to claim 18, wherein said recess of each radially widened portion is approximately half the thickness of the portion so that a combined thickness of superimposed radially widened portions of the semicircles is substantially equal to the overall thickness of the respective ring.

* * * * *